US00PP12126P2

(12) United States Plant Patent
Zary

(10) Patent No.: US PP12,126 P2
(45) Date of Patent: Oct. 9, 2001

(54) HYBRID TEA ROSE PLANT NAMED 'JACYELAP'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/405,424

(22) Filed: Sep. 22, 1999

(51) Int. Cl.[7] ..... A01H 5/00
(52) U.S. Cl. ..... Plt./130
(58) Field of Search ..... Plt./130, 132, 134, Plt./135

*Primary Examiner*—Howard J. Locker
(74) *Attorney, Agent, or Firm*—Klarquist Sparkman Campbell Leigh & Whinston, LLP

(57) ABSTRACT

A hybrid tea rose plant having vigorous, upright, well-branched growth; strong, healthy, dark green foliage; long cutting stems; and large, well-formed yellow-orange flowers.

1 Drawing Sheet

1

The present invention relates to a new and distinct variety of rose plant of the hybrid tea class which was originated by me by crossing two unnamed seedlings (not patented).

The primary objective of this breeding was to produce a new rose variety having the vigorous, upright growth, strong, healthy foliage and large flowers of the unnamed pink hybrid tea female parent, combined with the long stems, well formed flowers and healthy foliage of the unnamed yellow hybrid tea male parent. The objective was substantially achieved, along with other desirable improvements, as evidenced by the following unique combination of characteristics that are outstanding in the new variety and that distinguish it from its parents, as well as from all other varieties of which I am aware:

1. Novel, yellow-orange flower color;
2. Large, well formed blooms;
3. Healthy, dark green foliage;
4. Long cutting stems; and
5. Vigorous, upright, well-branched growth.

Asexual reproduction of this new variety by budding, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (unnamed seedling× JACtop — not patented).

*Pollen parent.*—Unnamed seedling (unnamed seedling×TANsenfrie — not patented).

Classification:

*Botanical.*—*Rosa hybrida.*

*Commercial.*—Hybrid Tea.

2

FLOWER

Observations made from specimens grown in a garden environment at Somis, Calif. from March 1998 to August 1999.

Blooming habit: Continuous.

Bud:

*Size.*—About 1¾ inches long when the petals start to unfurl.

*Form.*—The bud form is long; pointed ovoid.

*Color.*—When sepals first divide, bud color is Yellow-Orange Group 21D with the bud tip Orange-Red Group 34A. When half blown, the upper sides of the petals are Yellow-Orange Group 22D on the outer ⅓ of the petal, while the inner ⅔ of the petal is Yellow-Orange Group 16B. On the outer petal edge on the most open petals is a blush of Red Group 41C. The lower sides of the petals are Yellow-Orange Group 22D on the outer ¼ of the petal, with the rest of the surface Yellow-Orange Group 16B. On the outer edge of the most open petals is a blush of Red Group 41C.

*Sepals.*—Color: Green Group 138B with, on sepals exposed to bright sunlight, a cast of Greyed-Purple Group 184A. Surface texture: Covered in fine hairs. There are three lightly appendaged sepals. There are two unappendaged sepals with hairy edges.

*Receptacle.*—Color: Greep Group 137B unless exposed to bright sunlight, then there can be a blush of Greyed-Purple Group 184A. Shape: Funnel. Size: Medium (about ⅜"×3⁄16"). Surface: Smooth.

*Peduncle.*—Length: Medium (about 3 inches). Surface: Smooth. Color: Green Group 137C unless exposed to bright sunlight, then it can be Greyed-Purple Group 183A. Strength: Stiff; erect.

Bloom:

*Size.*—Large. Average open size is 5 inches.

*Borne.*—Singly.

*Stems.*—Strength: Strong. Average length is about 18–22 inches.

*Form.*—When first open, bloom is high centered. Permanence: Retains its form to the end; outer petals curl back.

*Petalage.*—Number of petals under normal conditions: 35.

*Color.*—The upper sides of the petals are Yellow-Orange Group 22D on the outer ⅓ of the petal, while the inner ⅔ are Yellow-Orange Group 16B. On the outer edge on the most open petals is a blush of Red Group 41C. The reverse sides of the petals are Yellow-Orange Group 22D on the outer ¼ of the petal with the rest of the surface Yellow-Orange Group 16B. On the outer edge of the most open petals is a blush of Red Group 41C. The base of each petal has on the upper surface a small, 3/16 inch×3/16 inch, Yellow Group 7A half moon at the point of attachment. The lower surface has a small, 1/16 inch× 1/16 inch Yellow Group 7A half moon at the point of attachment. The major color on the upper side is Yellow-Orange Group 16B.

*Variegations.*—Occasional greenish streak on the upper and lower surfaces along the midrib of the guard petals.

*Discoloration.*—The general tonality at the end of the first day: No change. At the end of the third day: No change. By day five or six, the petals will fade in color to Yellow-Orange Group 23D over their entire surface and then by day seven will drop.

*Fragrance.*—Moderate; apple.

Petals:

*Texture.*—Thick.

*Shape.*—Round to deltoid.

*Form.*—Tips slightly recurved; edges slightly quilled.

*Arrangement.*—Imbricated. There are no petaloids in the center.

*Persistence.*—Petals drop off cleanly before drying.

*Lastingness.*—On the plant: Long (about seven days). As a cut flower: Long (about eight days).

Reproductive parts:

*Anthers.*—Size: Medium. Quantity: Many. Color: Yellow-Orange Group 22C. Arrangement: Regular around styles.

*Filaments.*—Color: Orange-Red Group 34B.

*Pollen.*—Present.

*Styles.*—Color: Red-Purple Group 60A.

*Stigmas.*—Color: Orange-White Group 159A.

Plant:

*Form.*—Bush.

*Growth.*—Vigorous; upright; branching. At maturity, height is 5½ feet, width is 4½ feet.

Foliage: Number of leaflets on normal mid-stem leaves: Five.

*Size.*—Large (5 inches long×4 inches wide).

*Quantity.*—Abundant.

*Color.*—New foliage: Upper and lower surfaces: Greyed-Red Group 178A. Old foliage: Upper surface: Green Group 137A. Lower surface: Green Group 138B.

Leaflets:

*Shape.*—Pointed oval.

*Texture.*—Leathery; glossy.

*Edge.*—Serrated.

*Serration.*—Single; small.

*Petiole rachis.*—Color: Upper: Yellow-Green Group 146B with Greyed-Purple Group 183A on younger leaves. Lower: Yellow-Green Group 146C.

*Petiole underside.*—Smooth, with occasional prickles and glands.

*Stipules.*—Medium (about ½ inch), smooth, bearded and edged in glands.

*Disease resistance.*—Resistant to mildew and rust; susceptible to blackspot under normal growing conditions.

Wood:

*New wood.*—Color: Greyed-Purple Group 183C. Bark: Smooth.

*Old wood.*—Color: Green Group 137B. There can be some Greyed-Purple Group 183A on young canes but when fully mature, they are Green Group 137B. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 187B.

*Color when mature.*—Greyed-Orange Group 174C.

Small prickles:

*Quantity.*—On main stalks: None. On laterals: None.

I claim:

1. A new and distinct variety of rose plant of the hybrid tea class, substantially as herein shown and described, characterized particularly by its vigorous, upright, well-branched growth; strong, healthy, dark green foliage; long cutting stems; and large, well-formed yellow-orange flowers.

* * * * *

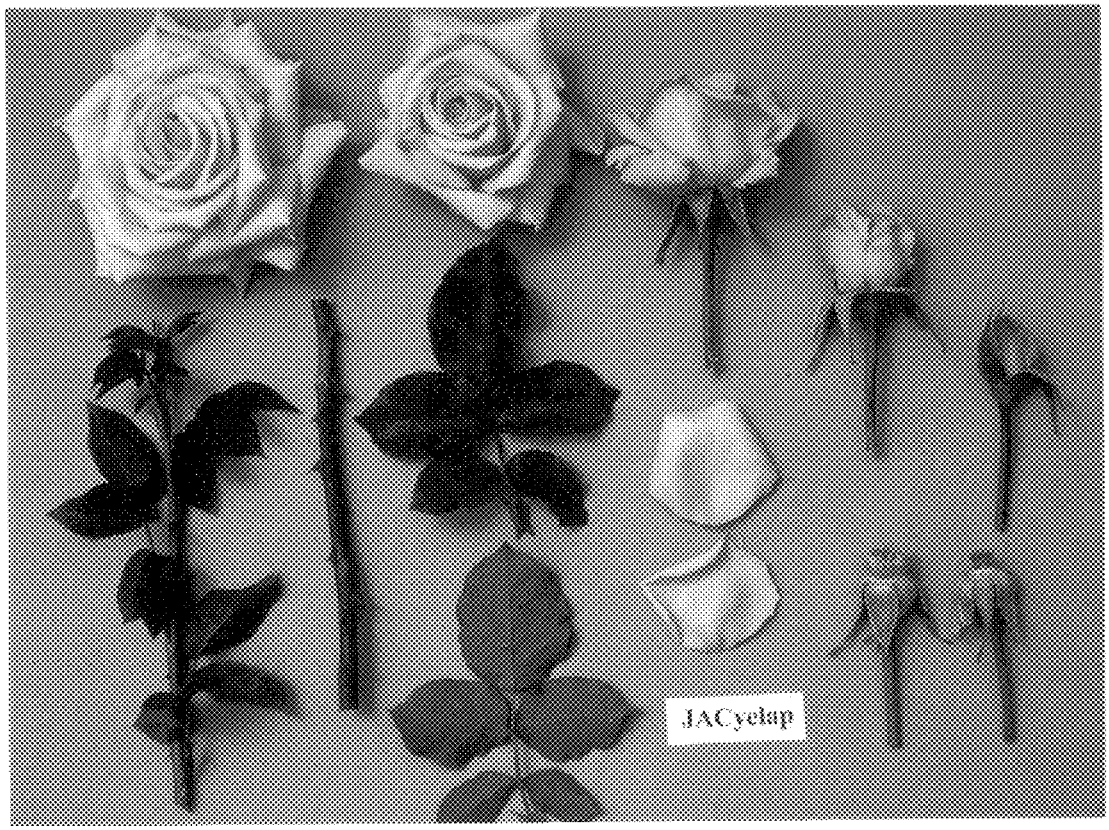
JACyclap